United States Patent
Wentkowski et al.

(10) Patent No.: US 6,430,439 B1
(45) Date of Patent: Aug. 6, 2002

(54) METHOD FOR COLLECTION OF BIVENTRICULAR HISTOGRAMS

(75) Inventors: Rene H. Wentkowski, White Bear Lake; Jeffrey E. Stahmann, Ramsey; James Kalgren, Lino Lakes, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/748,727

(22) Filed: Dec. 26, 2000

(51) Int. Cl.$^7$ .................................. A61N 1/37
(52) U.S. Cl. .......................................... 607/9
(58) Field of Search ................. 607/9, 30, 31, 607/32

(56) References Cited

U.S. PATENT DOCUMENTS

| | | | |
|---|---|---|---|
| 4,513,743 A | 4/1985 | van Arragon et al. | 128/419 |
| 4,928,688 A | 5/1990 | Mower | 128/419 PG |
| 5,088,488 A | 2/1992 | Morkowitz et al. | 128/419 |
| 5,797,970 A | 8/1998 | Pouvreau | 607/9 |
| 5,944,744 A | 8/1999 | Paul et al. | 607/9 |
| 5,948,005 A | 9/1999 | Valkai et al. | 607/32 |

*Primary Examiner*—Scott M. Getzow
(74) *Attorney, Agent, or Firm*—Schwegman, Lundberg, Woessner & Kluth, P.A.

(57) ABSTRACT

A method for operating a cardiac pacemaker in which paces and senses are counted during each cardiac cycle and associated with an R-R interval or other interval defining a cardiac cycle. An event frequency for each sense and pace is calculated which can be displayed as a histogram. The method is particularly suited for calculating such frequencies in resynchronization pacing modes.

16 Claims, 2 Drawing Sheets

METHOD FOR COLLECTION OF BIVENTRICULAR HISTOGRAMS

FIELD OF THE INVENTION

This invention pertains to cardiac rhythm management devices such as pacemakers. In particular, the invention relates to methods for data collection in such devices.

BACKGROUND

Cardiac pacemakers are cardiac rhythm management devices that provide electrical stimulation in the form of pacing pulses to selected chambers of the heart. (As the term is used herein, a pacemaker is any cardiac rhythm management device that performs cardiac pacing, including implantable cardioverter/defibrillators having a pacing functionality.) Cardiac rhythm management devices are typically implanted subcutaneously on a patient's chest and have leads threaded intravenously into the heart to connect the device to electrodes used for sensing and pacing, the electrodes being disposed in proximity to selected chambers of the heart. Pacemakers typically have a programmable electronic controller that causes the pacing pulses to be output in response to lapsed time intervals and sensed intrinsic cardiac activity.

The most common condition for which pacemakers are used is in the treatment of bradycardia, where the ventricular rate is too slow. If functioning properly, a pacemaker makes up for the heart's inability to pace itself at an appropriate rhythm in order to meet metabolic demand by enforcing a minimum heart rate. Pacing therapy can also be used in the treatment of congestive heart failure (CHF). It has also been shown that some CHF patients suffer from intraventricular and/or interventricular conduction defects such that their cardiac outputs can be increased by improving the synchronization of right and left ventricular contractions with electrical stimulation, referred to herein as ventricular resynchronization therapy.

Modern pacemakers also typically have the capability to communicate data via a radio-frequency link with an external programming device. Such data is transmitted to the pacemaker in order to program its mode of operation as well as define other operating parameters. Data is also transmitted from the pacemaker which can be used to verify the operating parameters as well as relay information regarding the condition of both the pacemaker and the patient. Among the data which may typically be telemetered from the pacemaker are the frequencies at which ventricular sensing and pacing events at particular R-R intervals occur, where an R-R interval is the time between ventricular events that define a cardiac cycle, either a ventricular sense or pace. Such data is typically displayed on the external programmer as a histogram.

SUMMARY OF THE INVENTION

The present invention relates to a method and system for calculating the frequencies at which sensing and pacing events occur for each channel of a cardiac rhythm management device. The method is particularly suited for calculating such event frequencies when the device is operated in a biventricular resynchronization pacing mode where, based upon senses from one ventricle designated as the rate chamber, paces are delivered to that ventricle and/or to the contralateral ventricle, designated the synchronized chamber. In accordance with the invention, paces and senses are counted during each cardiac cycle and associated with an R-R interval. A frequency of occurrence for each sense and pace is then calculated which can be displayed as a histogram. Pacing and sensing events are counted during each cardiac cycle for each sensing and pacing channel and associated with an R-R interval by assigning the event to an interval bin. An event frequency for each sense and pace is then calculated by dividing the sense and pace count in each bin by a denominator equal to the sum of the total sense counts for the rate chamber, the total pace counts for the rate chamber, and the total pace counts for the synchronized chamber only for those cardiac cycles in which no pace was delivered to the rate chamber. The method may be extended to cover multi-site synchronized pacing with a plurality of synchronized pacing channels, in which case only one synchronized pace is counted per cardiac cycle. Other embodiments may similarly be implemented to compute event frequencies for atrial events.

DESCRIPTION OF THE INVENTION

Among the useful data that may be collected by a pacemaker for later transmission to the external programmer are the frequencies that sensing and pacing events at particular R-R intervals occur. The present invention is directed toward a system and method for calculating such event frequencies in a pacemaker configured to deliver resynchronization therapy in accordance with multiple resynchronization pacing modes as described below.

1. Hardware Platform

Pacemakers are typically implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

Figure 1:
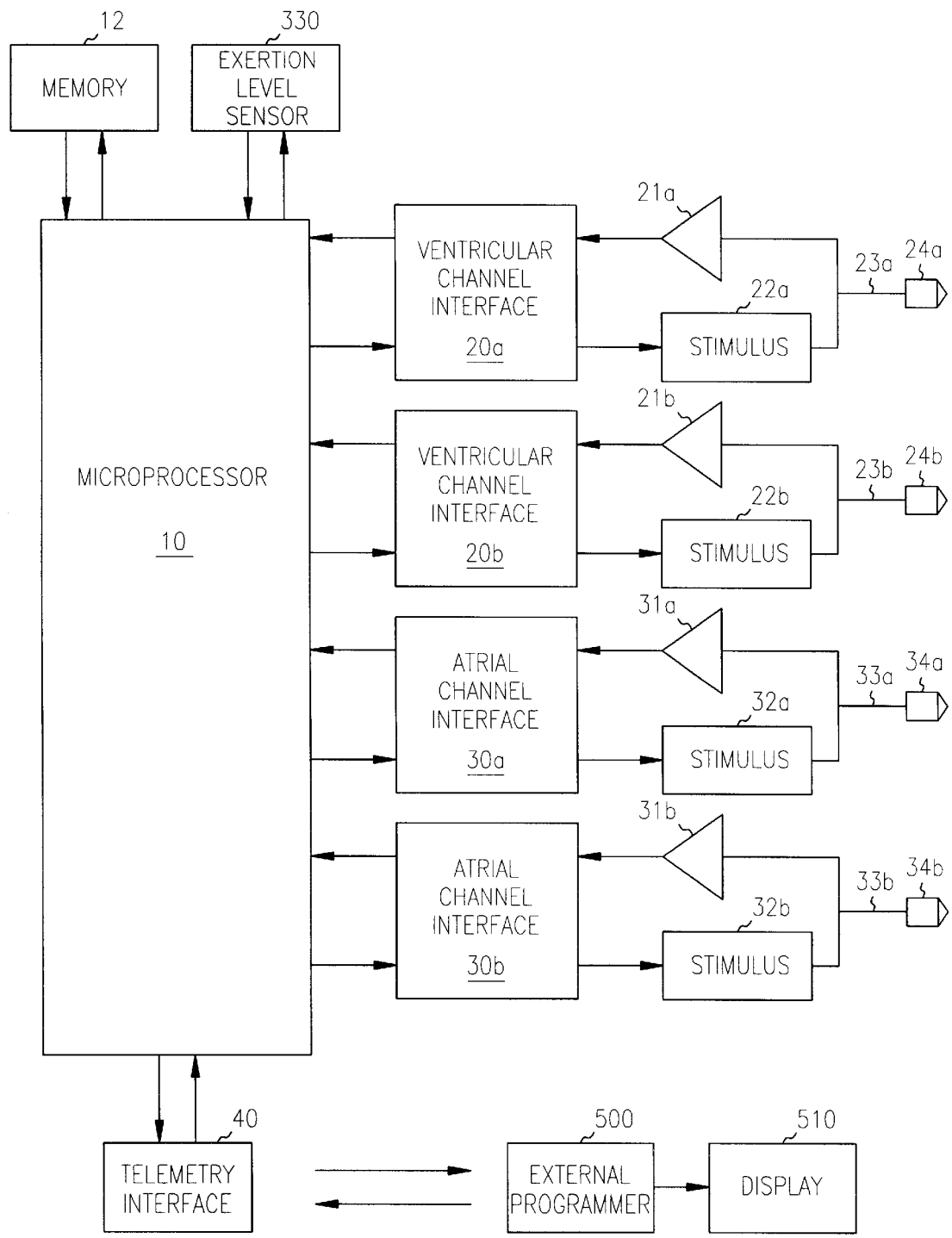
FIG. 1 is a system diagram of a microprocessor-based pacemaker.

FIG. 1 shows a system diagram of a microprocessor-based pacemaker physically configured with sensing and pacing channels for both atria and both ventricles. The controller 10 of the pacemaker is a microprocessor which communicates with a memory 12 via a bidirectional data bus. The memory 12 typically comprises a ROM (read-only memory) for program storage and a RAM (random-access memory) for data storage. The pacemaker has atrial sensing and pacing channels comprising electrode 34*a–b*, leads 33*a–b*, sensing amplifiers 31*a–b*, pulse generators 32*a–b*, and atrial channel interfaces 30*a–b* which communicate bidirectionally with microprocessor 10. The device also has ventricular sensing and pacing channels for both ventricles comprising electrodes 24*a–b*, leads 23*a–b*, sensing amplifiers 21*a–b*, pulse generators 22*a–b*, and ventricular channel interfaces 20*a–b*. In the figure, "a" designates one ventricular or atrial channel and "b" designates the channel for the contralateral chamber. In this embodiment, a single electrode is used for sensing and pacing in each channel, known as a unipolar lead. Other embodiments may employ bipolar leads which include two electrodes for outputting a pacing pulse and/or sensing intrinsic activity. The channel interfaces 20*a–b* and 30*a–b* include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. An exertion level sensor 330 (e.g., an accelerometer or a minute ventilation sensor) enables the controller to adapt the pacing rate in accordance with changes in the patient's physical activity. A telemetry interface 40 is also provided for communicating with an external programmer 500 which has an associated display 510. A pacemaker incorporating the present invention may possess all of the components in FIG. 1 and be programmable so as to operate in a number of different modes, or it may have only those components necessary to operate in a particular mode.

The controller 10 controls the overall operation of the device in accordance with programmed instructions stored in memory. The controller 10 controls the delivery of paces via the pacing channels, interprets sense signals from the sensing channels, implements timers for defining escape intervals and sensory refractory periods, and performs the pace counting functions as described below. It should be appreciated, however, that these functions could also be performed by custom logic circuitry either in addition to or instead of a programmed microprocessor.

2. Bradycardia Pacing Modes

Bradycardia pacing modes refer to pacing algorithms used to pace the atria and/or ventricles when the intrinsic atrial and/or ventricular rate is inadequate due to, for example, AV conduction blocks or sinus node dysfunction. Such modes may either be single-chamber pacing, where either an atrium or a ventricle is paced, or dual-chamber pacing in which both an atrium and a ventricle are paced. The modes are generally designated by a letter code of three positions where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used), and O (for no response). Modern pacemakers are typically programmable so that they can operate in any mode which the physical configuration of the device will allow. Additional sensing of physiological data allows some pacemakers to change the rate at which they pace the heart in accordance with some parameter correlated to metabolic demand. Such pacemakers are called rate-adaptive pacemakers and are designated by a fourth letter added to the three-letter code, R.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking pacemakers (i.e., VDD or DDD mode), another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing attempts to maintain the atrio-ventricular synchrony occurring with physiological beats whereby atrial contractions augment diastolic filling of the ventricles. If a patient has a physiologically normal atrial rhythm, atrial-tracking pacing also allows the ventricular pacing rate to be responsive to the metabolic needs of the body.

A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing (i.e., DDD mode), the lower rate limit interval is then the sum of the atrial escape interval and the atrio-ventricular interval.

Another type of synchronous pacing is atrial-triggered or ventricular-triggered pacing. In this mode, an atrium or ventricle is paced immediately after an intrinsic beat is detected in the respective chamber. Triggered pacing of a heart chamber is normally combined with inhibited demand pacing so that a pace is also delivered upon expiration of an escape interval in which no intrinsic beat occurs. Such triggered pacing may be employed as a safer alternative to asynchronous pacing when, due to far-field sensing of electromagnetic interference from external sources or skeletal muscle, false inhibition of pacing pulses is a problem. If a sense in the chamber's sensing channel is an actual depolarization and not a far-field sense, the triggered pace is delivered during the chamber's physiological refractory period and is of no consequence.

Finally, rate-adaptive algorithms may be used in conjunction with bradycardia pacing modes. Rate-adaptive pacemakers modulate the ventricular and/or atrial escape intervals based upon measurements corresponding to physical activity. Such pacemakers are applicable to situations in which atrial tracking modes cannot be used. In a rate-adaptive pacemaker operating in a ventricular pacing mode, for example, the LRL is adjusted in accordance with exertion level measurements such as from an accelerometer or minute ventilation sensor in order for the heart rate to more nearly match metabolic demand. The adjusted LRL is then termed the sensor-indicated rate.

3. Ventricular Resynchronization Therapy

Cardiac resynchronization therapy is pacing stimulation applied to one or more heart chambers in a manner that restores or maintains synchronized bilateral contractions of the atria and/or ventricles and thereby improves pumping efficiency. Certain patients with conduction abnormalities may experience improved cardiac synchronization with conventional single-chamber or dual-chamber pacing as described above. For example, a patient with left bundle branch block may have a more coordinated contraction of the ventricles with a pace than as a result of an intrinsic contraction. In that sense, conventional bradycardia pacing of an atrium and/or a ventricle may be considered as resynchronization therapy. Resynchronization pacing, however, may also involve pacing both ventricles and/or both atria in accordance with a synchronized pacing mode as described below. A single chamber may also be resynchronized to compensate for intra-atrial or intra-ventricular conduction delays by delivering paces to multiple sites of the chamber.

It is advantageous to deliver resynchronization therapy in conjunction with one or more synchronous bradycardia pacing modes, such as are described above. One atrium and/or one ventricle are designated as rate chambers, and paces are delivered to the rate chambers based upon pacing and sensed intrinsic activity in the chamber in accordance with the bradycardia pacing mode. In a single-chamber bradycardia pacing mode, for example, one of the paired atria or one of the ventricles is designated as the rate chamber. In a dual-chamber bradycardia pacing mode, either the right or left atrium is selected as the atrial rate chamber and either the right or left ventricle is selected as the ventricular rate chamber. The heart rate and the escape intervals for the pacing mode are defined by intervals between sensed and paced events in the rate chambers only. Resynchronization therapy may then be implemented by adding synchronized pacing to the bradycardia pacing mode where paces are delivered to one or more synchronized pacing sites in a defined time relation to one or more selected sensing and pacing events that either reset escape intervals or trigger paces in the bradycardia pacing mode. In bilateral synchronized pacing, which may be either biatrial or biventricular synchronized pacing, the heart chamber contralateral to the rate chamber is designated as a synchronized chamber. For example, the right ventricle may be designated as the rate ventricle and the left ventricle designated as the synchronized ventricle, and the paired atria may be similarly designated. Each synchronized chamber is then paced in a timed relation to a pace or sense occurring in the contralateral rate chamber.

One synchronized pacing mode may be termed offset synchronized pacing. In this mode, the synchronized chamber is paced with a positive, negative, or zero timing offset as measured from a pace delivered to its paired rate chamber, referred to as the synchronized chamber offset interval. The offset interval may be zero in order to pace both chambers simultaneously, positive in order to pace the synchronized chamber after the rate chamber, or negative to pace the synchronized chamber before the rate chamber. One example of such pacing is biventricular offset synchronized pacing where both ventricles are paced with a specified offset interval. The rate ventricle is paced in accordance with a synchronous bradycardia mode which may include atrial tracking, and the ventricular escape interval is reset with either a pace or a sense in the rate ventricle. (Resetting in this context refers to restarting the interval in the case of an LRL ventricular escape interval and to stopping the interval in the case of an AVI.) Thus, a pair of ventricular paces are delivered after expiration of the AVI escape interval or expiration of the LRL escape interval, with ventricular pacing inhibited by a sense in the rate ventricle that restarts the LRL escape interval and stops the AVI escape interval. In this mode, the pumping efficiency of the heart will be increased in some patients by simultaneous pacing of the ventricles with an offset of zero. However, it may be desirable in certain patients to pace one ventricle before the other in order to compensate for different conduction velocities in the two ventricles, and this may be accomplished by specifying a particular positive or negative ventricular offset interval.

Another synchronized mode is triggered synchronized pacing. In one type of triggered synchronized pacing, the synchronized chamber is paced after a specified trigger interval following a sense in the rate chamber, while in another type the rate chamber is paced after a specified trigger interval following a sense in the synchronized chamber. The two types may also be employed simultaneously. For example, with a trigger interval of zero, pacing of one chamber is triggered to occur in the shortest time possible after a sense in the other chamber in order to produce a coordinated contraction. (The shortest possible time for the triggered pace is limited by a sense-to-pace latency period dictated by the hardware.) This mode of pacing may be desirable when the intra-chamber conduction time is long enough that the pacemaker is able to reliably insert a pace before depolarization from one chamber reaches the other. Triggered synchronized pacing can also be combined with offset synchronized pacing such that both chambers are paced with the specified offset interval if no intrinsic activity is sensed in the rate chamber and a pace to the rate chamber is not otherwise delivered as a result of a triggering event. A specific example of this mode is ventricular triggered synchronized pacing where the rate and synchronized chambers are the right and left ventricles, respectively, and a sense in the right ventricle triggers a pace to the left ventricle and/or a sense in the left ventricle triggers a pace to the right ventricle.

As with other synchronized pacing modes, the rate chamber in a triggered synchronized pacing mode can be paced with one or more synchronous bradycardia pacing modes. If the rate chamber is controlled by a triggered bradycardia mode, a sense in the rate chamber sensing channel, in addition to triggering a pace to the synchronized chamber, also triggers an immediate rate chamber pace and resets any rate chamber escape interval. The advantage of this modal combination is that the sensed event in the rate chamber sensing channel might actually be a far-field sense from the synchronized chamber, in which case the rate chamber pace should not be inhibited. In a specific example, the right and left ventricles are the rate and synchronized chambers, respectively, and a sense in the right ventricle triggers a pace to the left ventricle. If right ventricular triggered pacing is also employed as a bradycardia mode, both ventricles are paced after a right ventricular sense has been received to allow for the possibility that the right ventricular sense was actually a far-field sense of left ventricular depolarization in the right ventricular channel. If the right-ventricular sense were actually from the right ventricle, the right ventricular pace would occur during the right ventricle's physiological refractory period and cause no harm.

As mentioned above, certain patients may experience some cardiac resynchronization from the pacing of only one ventricle and/or one atrium with a conventional bradycardia pacing mode. It may be desirable, however, to pace a single atrium or ventricle in accordance with a pacing mode based upon senses from the contralateral chamber. This mode, termed synchronized chamber-only pacing, involves pacing only the synchronized chamber based upon senses from the rate chamber. An example of synchronized chamber-only pacing is left ventricle-only synchronized pacing where the rate and synchronized chambers are the right and left ventricles, respectively. Left ventricle-only synchronized pacing may be advantageous where the conduction velocities within the ventricles are such that pacing only the left ventricle results in a more coordinated contraction by the ventricles than with conventional right ventricular pacing or biventricular pacing. Left ventricle-only synchronized pacing may be implemented in inhibited demand modes with or without atrial tracking, similar to biventricular pacing. A left ventricular pace is then delivered upon expiration of the AVI escape interval or expiration of the LRL escape interval, with left ventricular pacing inhibited by a right ventricular sense that restarts the LRL escape interval and stops the AVI escape interval.

In the synchronized modes described above, the rate chamber is synchronously paced with a mode based upon detected intrinsic activity in the rate chamber, thus protecting the rate chamber against paces being delivered during the vulnerable period. In order to provide similar protection to the synchronized chamber, a synchronized chamber protection period (SCPP) may be provided. The SCPP is a programmed interval which is initiated by sense or pace occurring in the synchronized chamber during which paces to the synchronized chamber are inhibited. For example, if the right ventricle is the rate chamber and the left ventricle is the synchronized chamber, a left ventricular protection period LVPP is triggered by a left ventricular sense which inhibits a left ventricular pace which would otherwise occur before the escape interval expires. The SCPP may be adjusted dynamically as a function of heart rate and may be different depending upon whether it was initiated by a sense or a pace. The SCPP provides a means to inhibit pacing of the synchronized chamber when a pace might be delivered during the vulnerable period or when it might compromise pumping efficiency by pacing the chamber too close to an intrinsic beat. In the case of a triggered mode where a synchronized chamber sense triggers a pace to the synchronized chamber, the pacing mode may be programmed to ignore the SCPP during the triggered pace. Alternatively, the mode may be programmed such that the SCPP starts only after a specified delay from the triggering event, which allows triggered pacing but prevents pacing during the vulnerable period.

In the case of synchronized chamber-only synchronized pacing, a synchronized chamber pace may be inhibited if a synchronized chamber sense occurs within a protection period prior to expiration of the rate chamber escape interval. Since the synchronized chamber pace is inhibited by the protection period, the rate chamber is not pseudo-paced and, if no intrinsic activity is sensed in the rate chamber, it will be paced upon expiration of the rate chamber escape intervals. The rate chamber pace in this situation may thus be termed a safety pace. For example, in left ventricle-only synchronized pacing, a right ventricular safety pace is delivered if the left ventricular pace is inhibited by the left ventricular protection period and no right ventricular sense has occurred.

Synchronized pacing may be applied to multiple sites of a single chamber. In these synchronized modes, one sensing/pacing channel is designated as the rate channel for sensing/pacing a rate site, and the other sensing/pacing channels in either the same or the contralateral chamber are designated as synchronized channels for sensing one or more synchronized sites. Pacing and sensing in the rate channel follows rate chamber timing rules, while pacing and sensing in the synchronized channels follows synchronized chamber timing rules as described above. The same or different synchronized pacing modes may be used in each synchronized channel.

3. Calculation of Sensing and Pacing Event Frequencies

Figure 2:
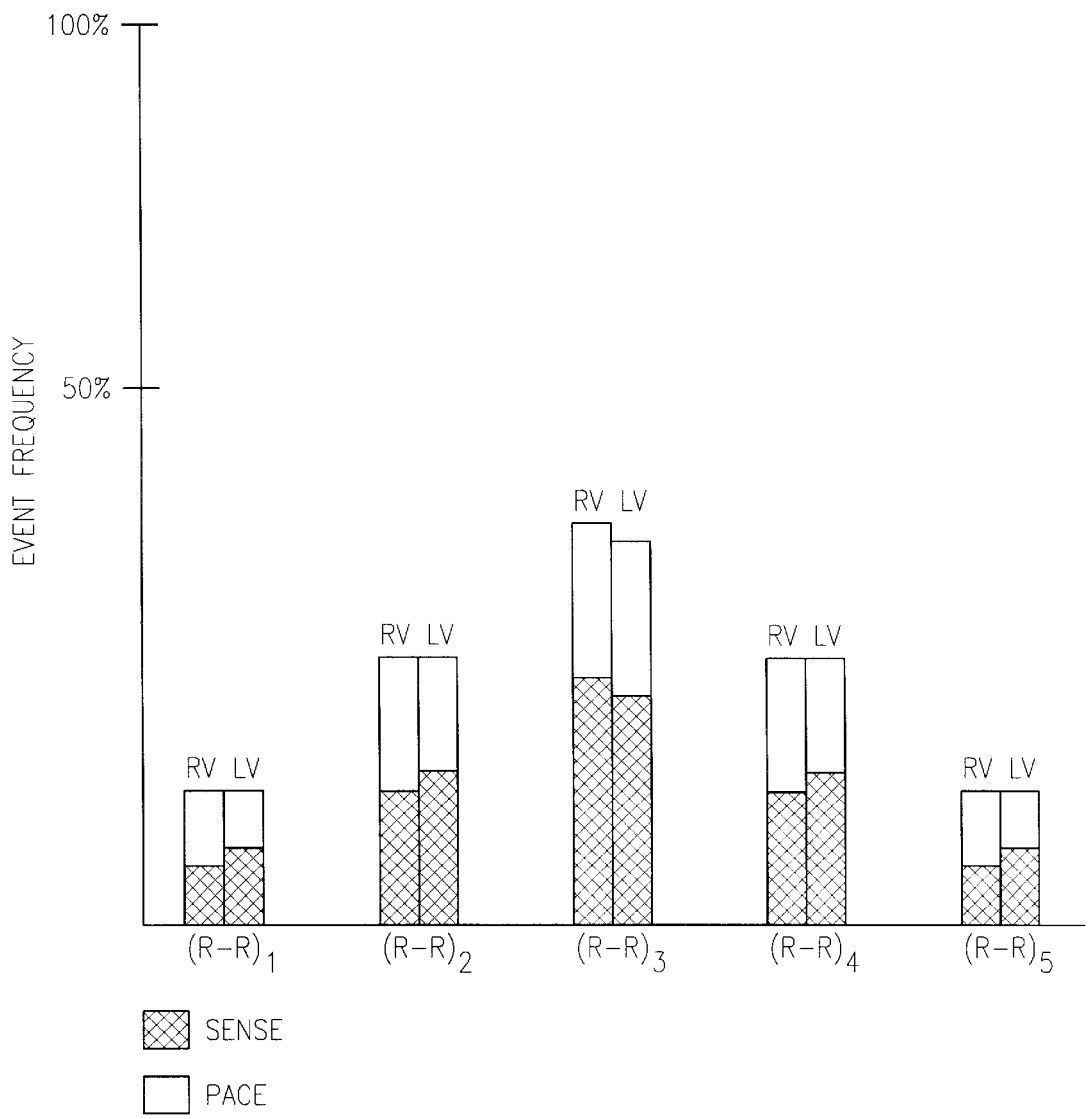
FIG. 2 is a histogram that displays frequencies of occurrence of senses and paces.

As noted above, it is useful for a clinician to have a record of the frequencies at which particular pacing and sensing events have occurred over a period of time. In the case of ventricular events, these event frequencies are the frequencies at which ventricular sensing and pacing events at particular R-R intervals occur, where an R-R interval is the time between ventricular events that define a cardiac cycle, either a ventricular sense or pace. Atrial event frequencies of atrial sensing and pacing events can similarly be recorded. FIG. 2 shows an example of a histogram representing such ventricular event frequencies as may be produced by a pacemaker operating in a biventricular pacing mode with pacing and sensing of both the right and left ventricles and where the R-R interval is the time between right ventricular events. In the diagram, each bar represents the frequency that ventricular sensing and pacing events occur at a particular R-R interval (each R-R interval actually represents a range of R-R intervals). A ventricular sense at a particular R-R interval corresponds to the instantaneous intrinsic ventricular rate. Ventricular paces occur at R-R intervals determined by the length of the ventricular escape interval which may either be constant or vary if atrial tracking and/or rate-adaptive pacing modes are used.

In order to collect the data to make up the histogram, the number of senses and paces occurring through the right ventricular channel are counted during each cardiac cycle for a specified period of time, and each counted sense or pace is assigned to an interval bin representing the R-R interval for that cardiac cycle. The event frequencies, which are expressed as a percentage of total cardiac cycles during the specified period of time, are calculated as follows:

%RVS in bin=RVS count in bin/total RVS count+total RVP count and

%RVP in bin=RVP count in bin/total RVS count+total RVP count where RVS is a right ventricular sense and RVP is a right ventricular pace. The denominator in each case is the total count of right ventricular senses and paces during the specified period of time. Since in an inhibited demand pacing mode based upon right ventricular senses, right ventricular senses and right ventricular paces are mutually exclusive for a given cardiac cycle, the denominator represents the total number of cardiac cycles. The formula thus correctly computes the frequency of occurrence for each sense and pace in a particular interval bin.

A pacemaker delivering resynchronization therapy may be capable of operating in a number of different resynchronization pacing modes and switched to different ones of those modes over a period of time, either automatically or as a result of reprogramming. It would be desirable for the device to use a method for computing event frequencies from event counts that would give consistent results over all of the different modes in which it might operate. Using a frequency formula with a denominator as set forth above, however, does not result in a correct computation of event frequencies when the pacemaker is operated in different resynchronization pacing modes. In a pacemaker operating in a resynchronization pacing mode, for example, the frequency of left ventricular senses could be calculated as:

%LVS in bin=LVS count in bin/total LVS count+total LVP count which gives an incorrect frequency if right ventricular pacing only is programmed since the denominator degenerates to just the total LVS count. Or, if biventricular pacing is programmed with a right ventricular sense frequency of 100% and loss of the left ventricular sensing, the denominator becomes zero.

The present invention is a method for computing event frequencies that produces consistent results over a plurality of different resynchronization pacing modes in which a rate chamber and/or one or more sites of a synchronized chamber are paced in accordance with events occurring in a rate chamber. In accordance with the invention, the number of senses and paces occurring in each rate and synchronized chamber are counted for a specified period of time, with each counted sense or pace assigned to an interval bin representing the rate chamber event interval for the cardiac cycle in which the event occurred. The rate chamber event interval is the time between rate chamber events that define a cardiac cycle, either a sense or pace. The event frequency for the senses and paces in each interval bin over the specified period of time is then calculated by dividing the sense and pace count in each bin by a denominator equal to the sum of the total sense counts for the rate chamber, the total pace counts for the rate chamber, and the total pace counts for the synchronized chamber only for those cardiac cycles in which no pace was delivered to the rate chamber. The denominator then correctly corresponds to the total number of cardiac cycles and is calculated solely from event counts. In a resynchronization mode where multiple synchronized channels are employed, only one synchronized chamber pace is counted per cardiac cycle if one or more occurs when no pace is delivered to the rate chamber. The method may be applied to compute event frequencies for either ventricular or atrial events.

In an exemplary embodiment, the pacemaker is operated in a resynchronization pacing mode such that the right ventricle is the rate chamber and the left ventricle is the synchronized chamber. In these modes, only the left ventricle or both ventricles may be paced in an inhibited demand mode based only upon right ventricular senses with left ventricular senses used only to inhibit left ventricular paces. Each event is assigned to an interval bin representing a rate chamber event interval, which in this case is the R-R interval as measured with respect to right ventricular senses or paces. The formula for computing event frequencies then becomes:

%event in bin=event count in bin/total RVS count+total RVP count+total LVP count where the LVP count includes only those left ventricular pacing events in which no right ventricular pace is delivered for that cardiac cycle.

In a system incorporating the invention as described above, the computation of event frequencies may be performed by the controller of a cardiac rhythm management device and then transmitted to an external programmer for display. Alternatively, the raw counts of each event may be transmitted to the external programmer which then performs the computations to derive the event frequencies for each event.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating a cardiac pacemaker in resynchronization pacing mode, comprising:
   sensing rate and synchronized heart chambers through separate channels and generating sense signals upon detection of depolarization occurring in a chamber;
   pacing the rate chamber in accordance with bradycardia pacing mode based upon rate chamber senses and paces;
   pacing the synchronized chamber in accordance with a resynchronization pacing mode;
   measuring a rate chamber event interval for each cardiac cycle, wherein the interval is the time between rate chamber senses and paces that define a cardiac cycle;
   counting the number of senses and paces occurring in each rate and synchronized chamber for a specified period of time and assigning each counted sense or pace to an interval bin representing the rate chamber event interval for that cardiac cycle so that each interval bin contains a sense count and a pace count for each chamber;
   calculating an event frequency for the senses and paces in each interval bin over the specified period of time by dividing the sense and pace count in each bin by a denominator equal to the sum of the total sense counts for the rate chamber, the total pace counts for the rate chamber, and the total pace counts for the synchronized chamber only for those cardiac cycles in which no pace was delivered to the rate chamber.

2. The method of claim 1 wherein the rate and synchronized chambers are the right and left ventricles, respectively, and the rate chamber event interval is an R-R interval.

3. The method of claim 2 wherein the R-R interval is measured with respect to right ventricular senses and paces.

4. The method of claim 1 wherein the rate and synchronized chambers are the right and left atria, respectively.

5. The method of claim 1 further comprising sensing and pacing the synchronized chamber through one or more additional synchronized channels and wherein the event frequency for the senses and paces in each interval bin over the specified period of time is calculated by dividing the sense and pace count in each bin by a denominator equal to the sum of the total sense counts for the rate chamber, the total pace counts for the rate chamber, and the total pace counts for the synchronized chamber only for those cardiac cycles in which no pace was delivered to the rate chamber, where only one synchronized chamber pace is counted per cardiac cycle if one or more occurs.

6. A cardiac rhythm management device, comprising:
   sensing channels for sensing depolarizations in a pair of heart chambers and generating sense signals in accordance therewith;
   right and left pacing channels for delivering paces to the right and left chambers, wherein one chamber is designated as the synchronized chamber and the other chamber as the rate chamber;
   a controller for controlling the delivery of paces to the rate chamber in accordance with a bradycardia pacing mode and to pace the synchronized chamber in accordance with a resynchronization pacing mode;
   wherein the controller is programmed to measure a rate chamber event interval for each cardiac cycle, wherein the interval is the time between rate chamber senses and paces that define a cardiac cycle, and to count the number of senses and paces occurring in each rate and synchronized chamber for a specified period of time and assign each counted sense or pace to an interval bin representing the rate chamber event interval for that cardiac cycle so that each interval bin contains a sense count and a pace count for each chamber; and, wherein the controller is programmed to calculate an event frequency for the senses and paces in each interval bin over the specified period of time by dividing the sense and pace count in each bin by a denominator equal to the sum of the total sense counts for the rate chamber, the total pace counts for the rate chamber, and the total pace counts for the synchronized chamber only for those cardiac cycles in which no pace was delivered to the rate chamber.

7. The device of claim 6 wherein the rate and synchronized chambers are the right and left ventricles, respectively, and the rate chamber event interval is an R-R interval.

8. The device of claim 7 wherein the controller is programmed to measure the R-R interval with respect to right ventricular senses and paces.

9. The device of claim 6 wherein the rate and synchronized chambers are the right and left atria, respectively.

10. The device of claim 6 further comprising one or more additional synchronized channels and wherein the controller is programmed to calculate the event frequency for the senses and paces in each interval bin over the specified period of time by dividing the sense and pace count in each bin by a denominator equal to the sum of the total sense counts for the rate chamber, the total pace counts for the rate chamber, and the total pace counts for the synchronized chamber only for those cardiac cycles in which no pace was delivered to the rate chamber, where only one synchronized chamber pace is counted per cardiac cycle if one or more occurs.

11. The device of claim 6 further comprising a telemetry interface and wherein the controller is programmed to transmit the event frequencies for senses and paces in each interval bin as a percentage of cardiac cycles to an external programmer.

12. A cardiac rhythm management system, comprising:
an external programmer;
a pacemaker having sensing channels for sensing depolarizations in a pair of heart chambers and generating sense signals in accordance therewith, right and left pacing channels for delivering paces to the right and left chambers, wherein one chamber is designated as the synchronized chamber and the other chamber as the rate chamber, a controller for controlling the delivery of paces to the rate chamber in accordance with a bradycardia pacing mode and to pace the synchronized chamber in accordance with a resynchronization pacing mode, and a telemetry interface for transmitting data to the external programmer;

wherein the pacemaker controller is programmed to measure a rate chamber event interval for each cardiac cycle, wherein the interval is the time between rate chamber senses and paces that define a cardiac cycle, and to count the number of senses and paces occurring in each rate and synchronized chamber for a specified period of time and assign each counted sense or pace to an interval bin representing the rate chamber event interval for that cardiac cycle so that each interval bin contains a sense count and a pace count for each chamber;

wherein the controller is programmed to transmit the counts in each interval bin to an external programmer; and, wherein the external programmer is configured to calculate an event frequency for the senses and paces in each interval bin over the specified period of time by dividing the sense and pace count in each bin by a denominator equal to the sum of the total sense counts for the rate chamber, the total pace counts for the rate chamber, and the total pace counts for the synchronized chamber only for those cardiac cycles in which no pace was delivered to the rate chamber.

13. The system of claim 12 wherein the rate and synchronized chambers are the right and left ventricles, respectively, and the rate chamber event interval is an R-R interval.

14. The system of claim 13 wherein the controller is programmed to measure the R-R interval with respect to right ventricular senses and paces.

15. The system of claim 12 wherein the rate and synchronized chambers are the right and left atria, respectively.

16. The device of claim 12 further comprising one or more additional synchronized channels and wherein the external programmer is configured to calculate the event frequency for the senses and paces in each interval bin over the specified period of time by dividing the sense and pace count in each bin by a denominator equal to the sum of the total sense counts for the rate chamber, the total pace counts for the rate chamber, and the total pace counts for the synchronized chamber only for those cardiac cycles in which no pace was delivered to the rate chamber, where only one synchronized chamber pace is counted per cardiac cycle if one or more occurs.

* * * * *

UNITED STATES PATENT AND TRADEMARK OFFICE
CERTIFICATE OF CORRECTION

PATENT NO. : 6,430,439 B1
DATED : August 6, 2002
INVENTOR(S) : James Kalgren, Jeffrey E. Stahmann and Rene H. Wentkowski It is certified that error appears in the above-identified patent and that said Letters Patent is hereby corrected as shown below:

<u>Title page,</u>
Item [75], Inventors, delete "White Bear Lake;" after "Rene H. Wentkowski," and insert -- Overizse, Belgium; --, therefor.

Signed and Sealed this

Twenty-ninth Day of July, 2003

JAMES E. ROGAN
*Director of the United States Patent and Trademark Office*